US00PP34241P2

(12) United States Plant Patent
Pakozdi et al.

(10) Patent No.: US PP34,241 P2
(45) Date of Patent: May 17, 2022

(54) STRAWBERRY PLANT NAMED 'DRISSTRAWEIGHTYEIGHT'

(50) Latin Name: ***Fragaria* x *ananassa***
Varietal Denomination: DrisStrawEightyEight

(71) Applicant: Driscoll's, Inc., Watsonville, CA (US)

(72) Inventors: Katalin M. Pakozdi, Watsonville, CA (US); Alessandra Lillo, Watsonville, CA (US); Katarzyna Blake, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/211,413

(22) Filed: Mar. 24, 2021

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr. et al.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson et al.
PP22,247 P2 11/2011 Ferguson
PP23,107 P2 10/2012 Ferguson et al.
PP23,148 P2 10/2012 Gilford et al.
PP23,377 P2 2/2013 Ferguson et al.
PP23,378 P2 2/2013 Pullen et al.
PP23,382 P2 2/2013 Ferguson et al.
PP23,383 P2 2/2013 Ferguson et al.
PP23,400 P2 2/2013 Ferguson et al.
PP23,401 P2 2/2013 Pullen et al.
PP23,459 P2 3/2013 Stewart et al.
PP23,506 P3 4/2013 Ferguson et al.
PP23,517 P3 4/2013 Ferguson et al.
PP24,096 P3 12/2013 Fear et al.

(Continued)

*Primary Examiner* — Kent L Bell
(74) *Attorney, Agent, or Firm* — Morrison & Foerster LLP

(57) ABSTRACT

A new and distinct variety of strawberry plant named 'DrisStrawEightyEight', particularly selected for its upright architecture, fruit yield, fruit size, fruit appearance, shelf life, and relatively low cull rate, is disclosed.

3 Drawing Sheets

(56) References Cited

U.S. PATENT DOCUMENTS

| | | | |
|---|---|---|---|
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| PP30,775 | P2 | 8/2019 | Carrillo Mendoza et al. |
| PP30,789 | P2 | 8/2019 | Ferguson et al. |
| PP30,818 | P2 | 8/2019 | Pakozdi et al. |
| PP30,851 | P2 | 8/2019 | Fear et al. |
| PP30,936 | P2 | 10/2019 | Stewart et al. |
| PP31,083 | P2 | 11/2019 | Carrillo Mendoza et al. |
| PP31,233 | P2 | 12/2019 | Pakozdi et al. |
| PP31,527 | P3 | 3/2020 | Carrillo Mendoza et al. |
| PP31,655 | P2 | 4/2020 | Carrillo Mendoza et al. |
| PP31,703 | P2 | 4/2020 | Stewart et al. |
| PP31,827 | P2 | 6/2020 | Ferguson et al. |
| PP31,896 | P2 | 6/2020 | Pakozdi et al. |
| PP31,935 | P2 | 7/2020 | Pakozdi et al. |
| PP32,079 | P2 | 8/2020 | Carrillo Mendoza et al. |
| PP32,080 | P2 | 8/2020 | Ferguson et al. |
| PP32,271 | P2 | 10/2020 | Ferguson et al. |
| PP32,305 | P3 | 10/2020 | Pakozdi et al. |
| PP32,498 | P2 | 11/2020 | Carrillo Mendoza et al. |
| PP32,499 | P3 | 11/2020 | Jacobs et al. |
| PP32,500 | P3 | 11/2020 | Stewart et al. |
| PP32,801 | P2 | 2/2021 | Ferguson et al. |
| PP32,814 | P2 | 2/2021 | Stewart et al. |
| PP32,824 | P2 | 2/2021 | Stewart et al. |
| 2003/0079263 | P1 | 4/2003 | Gilford et al. |
| 2013/0276182 | P1 | 10/2013 | Fear et al. |

STRAWBERRY PLANT NAMED 'DRISSTRAWEIGHTYEIGHT'

Latin name:

Botanical classification: *Fragaria* x *ananassa.*

Varietal denomination: The varietal denomination of the claimed variety of strawberry plant is 'DrisStrawEightyEight'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawEightyEight'.

Strawberry plant variety 'DrisStrawEightyEight' was discovered in East Malling, Kent, United Kingdom in June of 2015 and originated from a cross between the proprietary female parent 'UUK 143-002' (unpatented) and the proprietary male parent 'VUK 085-005' (unpatented). The original seedling of the new variety was first asexually propagated in the Netherlands via stolons in July of 2015.

'DrisStrawEightyEight' was subsequently asexually propagated via stolons, and has undergone testing at test plots in East Malling, Kent, United Kingdom for five years (2015 to 2020). The present variety has been found to be stable and reproduce true to type through successive asexual propagations via stolons and tissue culture.

'DrisStrawEightyEight' was particularly selected for its upright architecture, fruit yield, fruit size, fruit appearance, shelf life, and relatively low cull rate.

DESCRIPTION OF THE DRAWINGS

This new strawberry plant is illustrated by the accompanying photographs. The colors shown are as true as can be reasonably obtained by conventional photographic procedures. Unless otherwise indicated, the photographs are of plants that are nine to eleven months old.

DETAILED BOTANICAL DESCRIPTION

Figure 1:
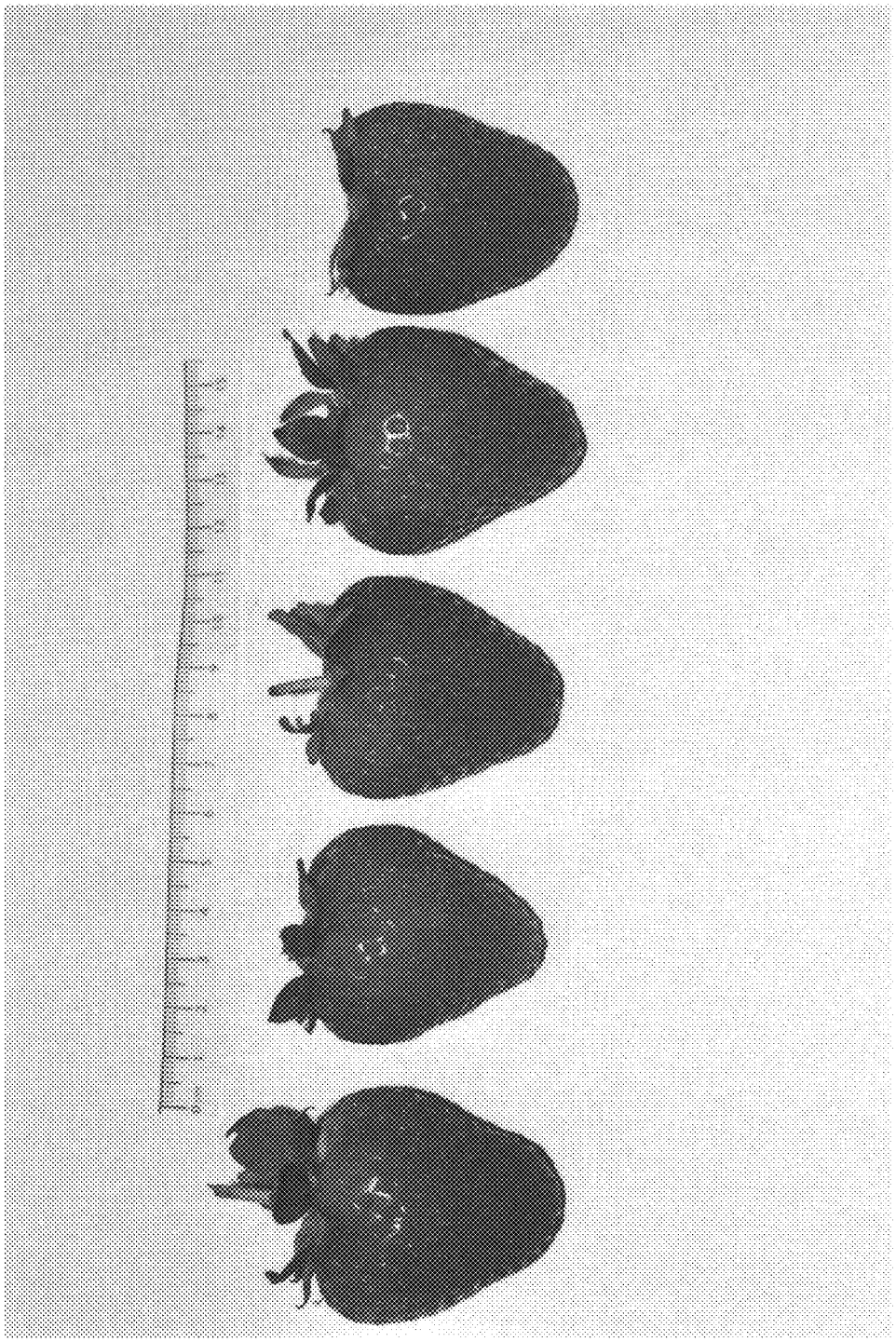
FIG. 1 illustrates whole fruit of variety 'DrisStrawEightyEight'.
Figure 2:
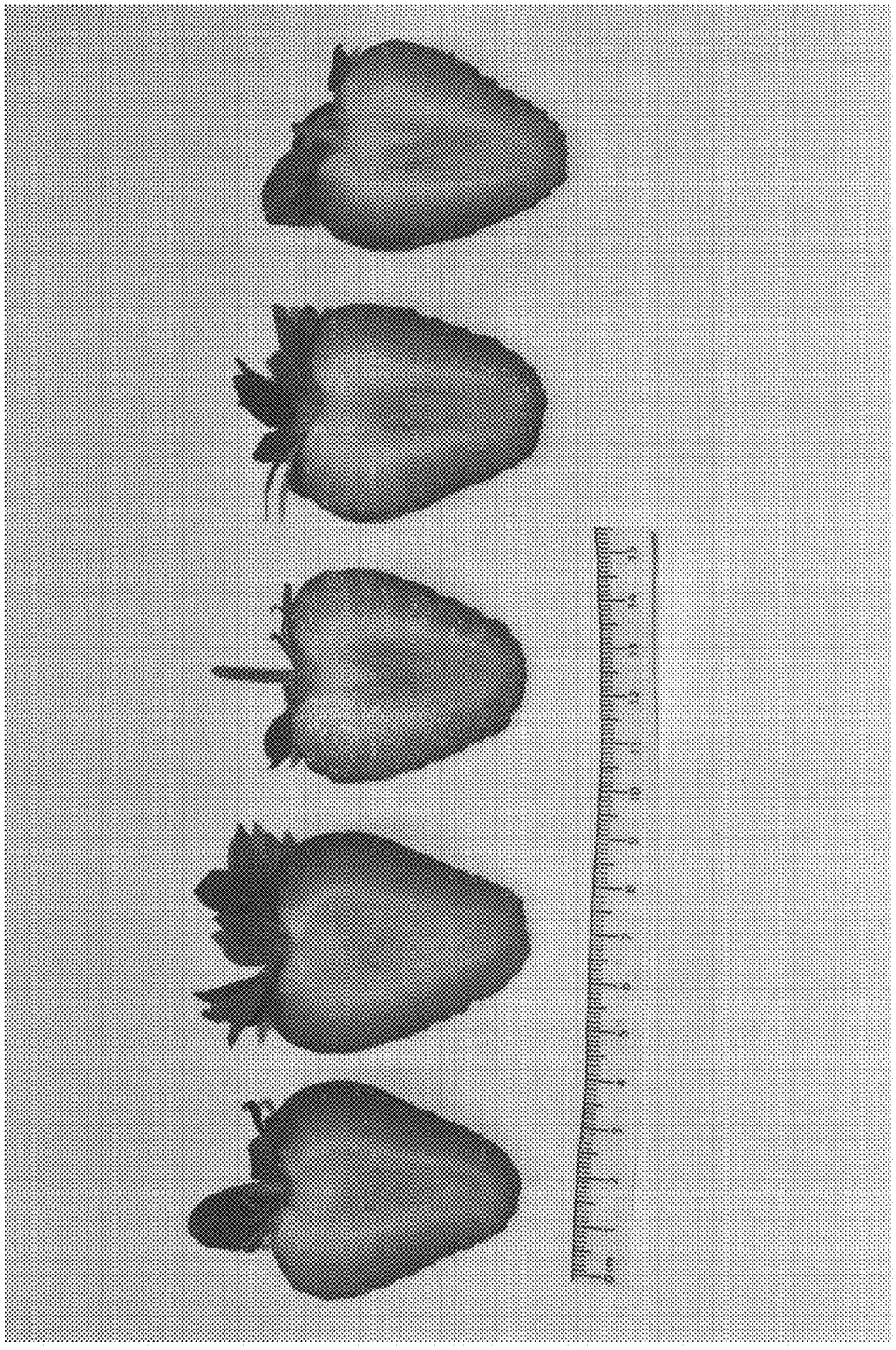
FIG. 2 illustrates longitudinal sections of fruit of variety 'DrisStrawEightyEight'.
Figure 3:
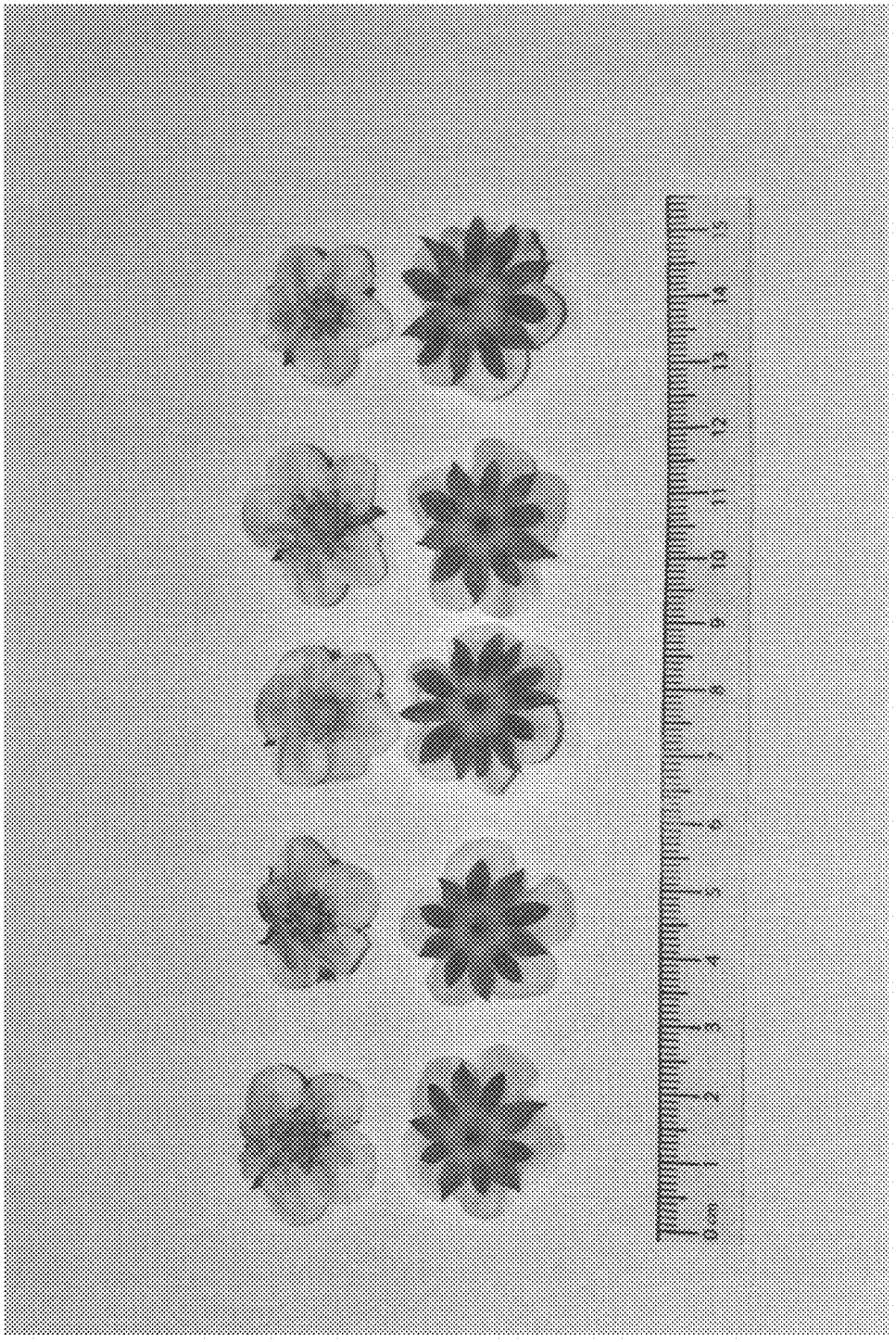
FIG. 3 illustrates the upper surface (top row) and lower surface (bottom row) of flowers of variety 'DrisStrawEightyEight'.

The following detailed descriptions set forth the distinctive characteristics of 'DrisStrawEightyEight'. The data which define these characteristics is based on observations taken in East Malling, Kent, United Kingdom from 2015 to 2020. This description is in accordance with UPOV terminology. Color designations, color descriptions, and other phenotypical descriptions may deviate from the stated values and descriptions depending upon variation in environmental, seasonal, climatic, and cultural conditions. 'DrisStrawEightyEight' has not been observed under all possible environmental conditions. The botanical description of 'DrisStrawEightyEight' was taken from plants that were nine to eleven months old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

- *Species.*—*Fragaria* x *ananassa.*
- *Common name.*—Strawberry.
- *Denomination.*—'DrisStrawEightyEight'.

Parentage:

- *Female parent.*—Proprietary strawberry plant 'UUK 143-002' (unpatented).
- *Male parent.*—Proprietary strawberry plant 'VUK 085-005' (unpatented).

Plant:

- *Height.*—44.35 cm.
- *Diameter.*—38 cm.
- *Number of crowns per plant.*—6.6.
- *Growth habit.*—Upright.
- *Density of foliage.*—Medium.
- *Vigor.*—Strong.

Stolon:

- *Number of daughter plants per square foot.*—13.5.
- *Diameter at bract.*—3.79 mm.
- *Anthocyanin coloration.*—Medium to strong.
- *Stolon color with anthocyanin coloration.*—RHS 145A (Strong yellow green).
- *Density of pubescence.*—Sparse.

Leaf:

- *Number of leaflets.*—Three only.
- *Color of upper surface.*—RHS N134A (Dark yellowish green).
- *Color of lower surface.*—RHS 138B (Moderate yellow green).
- *Blistering.*—Medium.
- *Glossiness.*—Strong.
- *Variegation.*—Absent.
- *Terminal leaflet.*—Length: 10.9 cm. Width: 11.9 cm. Length/width ratio: 0.9. Number of teeth per terminal leaflet: 17.5. Shape of base: Obtuse. Shape of apex: Rounded. Margin: Serrate to crenate. Shape in cross section: Concave.

*Petiole*.—Length: 38.3 cm. Diameter: 4.7 mm. Attitude of hairs: Slightly outwards. Bract frequency (number present on each petiole): 0. Color: RHS 145A (Strong yellow green).

*Petiolule*.—Length: 7.5 mm. Diameter: 3.04 mm. Surface texture: Rugose. Color: RHS 145B (Light yellow green).

*Stipule*.—Length: 3.48 cm. Width: 9.8 mm. Anthocyanin coloration: Weak. Anthocyanin color: RHS 39B (Deep yellowish pink). Overall color: RHS 146D (Moderate yellow green).

Inflorescence:

*Number of flowers per plant*.—31.9.

*Position of inflorescence in relation to foliage*.—Above.

*Pedicel*.—Attitude of hairs: Slightly outwards. Length: 4 cm. Diameter: 3 mm. Color: RHS 144B (Strong yellow green).

*Flower*.—Flower diameter (petal tip to petal tip on non-flattened flower): 24.5 mm. Flower depth: 13 mm. Arrangement of petals: Overlapping. Size of calyx in relation to corolla: Same size. Stamen: Present.

*Petal*.—Length: 9.39 mm. Width: 10.74 mm. Length/width ratio: 0.9. Number of petals per flower: 5.3. Color of upper side: RHS 155B (Yellowish white). Color of lower side: RHS 155C (Greenish white). Texture of upper surface: Smooth. Texture of lower surface: Smooth. Base shape: Rounded. Apex shape: Concavo-convex. Margin type: Entire.

*Calyx*.—Diameter (sepal tip to sepal tip, measured on back of flower): 21.4 mm.

*Sepal*.—Length: 4.91 mm. Width: 4.9 mm. Number of sepals per flower: 5.3. Color of upper side: RHS 139B (Moderate yellowish green). Color of lower side: RHS 141C (Strong yellowish green). Texture of upper surface: Glabrous. Texture of lower surface: Pubescent. Apex shape: Acuminate. Margin type: Entire.

*Flowering*.—Flowering interval: Late April to mid-June.

Fruit:

*Fruit size*.—Length: 52.6 mm. Width: 44.9 mm. Length/width ratio: 1.1. Individual fruit weight: 28.4 g.

*Fruit hollow*.—Length: 24.6 mm. Width: 11.5 mm. Length/width ratio: 2.1.

*Shape*.—Cordate.

*Difference in shape of terminal and other fruits*.—None or very slight.

*Fruit color*.—RHS N34B (Strong reddish orange).

*Evenness of color*.—Even or very slightly uneven.

*Glossiness*.—Medium.

*Evenness of surface*.—Even or very slightly uneven.

*Width of band without achenes*.—Absent or very narrow.

*Position of achenes*.—Below surface.

*Number of achenes per fruit*.—250.

*Achene color*.—RHS 11A (Brilliant yellow).

*Position of calyx attachment*.—Inserted.

*Attitude of sepals*.—Upwards.

*Diameter of calyx in relation to diameter of fruit*.—Slightly smaller.

*Adherence of calyx*.—Medium.

*Firmness*.—Firm.

*Color of flesh* (*excluding core*).—RHS N45B (Moderate red).

*Color of core*.—RHS 42C (Strong reddish orange).

*Fruiting*.—Harvest interval: Early May to late June. Type of bearing: Not remontant. Productivity: 0.640 kg of fruit per plant per season from nine- to eleven-month-old plants when grown in East Malling, Kent, United Kingdom.

*Storage characteristics* (*post-harvest characteristics*).—Following harvest, fruit can be stored for 7-10 days if maintained under cooled temperatures that are standard for strawberry storage.

Resistance to diseases:

*Powdery mildew* (*podosphaera macularis*).—Susceptible.

*Verticillium wilt* (*verticillium dahliae*).—Moderately susceptible.

COMPARISON WITH PARENTAL AND REFERENCE VARIETIES

'DrisStrawEightyEight' differs from the proprietary female parent 'UUK 143-002' (unpatented) in that plants of 'DrisStrawEightyEight' are more productive when compared with plants of 'UUK 143-002'. In addition, fruit of 'DrisStrawEightyEight' is much larger than fruit of 'UUK 143-002'.

'DrisStrawEightyEight' differs from the proprietary male parent 'VUK 085-005' (unpatented) in that plants of 'DrisStrawEightyEight' are higher yielding and produce significantly less culls (non-marketable fruit) when compared with plants of 'VUK 085-005'. Further, fruit of 'DrisStrawEightyEight' are larger, sweeter, and have a significantly improved shelf life when compared with fruit of 'VUK 085-005'.

'DrisStrawEightyEight' differs from the reference variety 'DrisStrawSeventyTwo' (U.S. Plant Pat. No. 31,896) in that 'DrisStrawEightyEight' has improved yield and shelf life when compared to 'DrisStrawSeventyTwo'. Further, 'DrisStrawEightyEight' has an inserted position of calyx attachment on fruit, inflorescence above foliage, an overlapping arrangement of flower petals, and a cordate shape of fruit, whereas 'DrisStrawSeventyTwo' has a position of calyx attachment that is level with fruit, inflorescence same level as foliage, a free arrangement of flower petals, and a conical shape of fruit.

What is claimed is:

1. A new and distinct variety of strawberry plant named 'DrisStrawEightyEight' as shown and described herein.

* * * * *